(12) United States Patent
Sato

(10) Patent No.: US 11,331,075 B2
(45) Date of Patent: May 17, 2022

(54) ULTRASONIC SENSOR AND ULTRASONIC SENSOR DEVICE

(71) Applicant: KYOCERA Corporation, Kyoto (JP)

(72) Inventor: Yohei Sato, Osaka (JP)

(73) Assignee: KYOCERA CORPORATION, Kyoto (JP)

( * ) Notice: Subject to any disclaimer, the term of this patent is extended or adjusted under 35 U.S.C. 154(b) by 439 days.

(21) Appl. No.: 16/491,330

(22) PCT Filed: Mar. 1, 2018

(86) PCT No.: PCT/JP2018/007832
§ 371 (c)(1),
(2) Date: Sep. 5, 2019

(87) PCT Pub. No.: WO2018/163963
PCT Pub. Date: Sep. 13, 2018

(65) Prior Publication Data
US 2020/0029936 A1    Jan. 30, 2020

(30) Foreign Application Priority Data
Mar. 9, 2017    (JP) .............................. JP2017-044681

(51) Int. Cl.
*A61B 8/14* (2006.01)
*A61B 8/00* (2006.01)
*B06B 1/06* (2006.01)
*H04R 17/00* (2006.01)

(52) U.S. Cl.
CPC .............. *A61B 8/4483* (2013.01); *A61B 8/14* (2013.01); *B06B 1/0622* (2013.01); *B06B 1/0651* (2013.01); *H04R 17/00* (2013.01); *B06B 2201/55* (2013.01)

(58) Field of Classification Search
CPC ....... A61B 8/14; A61B 8/4483; B06B 1/0622; B06B 1/0651; B06B 1/0696; B06B 2201/55; B06B 2201/76; H04R 17/00
See application file for complete search history.

(56) References Cited

U.S. PATENT DOCUMENTS 10,751,755 B1 *  8/2020  Horsley ................. H01L 41/09

FOREIGN PATENT DOCUMENTS

| JP | 2013-135793 A | 7/2013 | |
| WO | WO-2016054448 A1 * | 4/2016 | .......... B06B 1/0662 |
| WO | WO-2016061410 A1 * | 4/2016 | .......... B06B 1/0207 |

* cited by examiner

*Primary Examiner* — Mark D Remaly
(74) *Attorney, Agent, or Firm* — Volpe Koenig

(57) ABSTRACT

A sensor includes a first element part and a second element part. The first element part includes a first upper main electrode part, a first upper sub electrode part and a first lower electrode layer. In the second element part, a configuration of electrodes is inverse to that of the first element part. It includes a second lower main electrode part, a second lower sub electrode part and a second upper electrode layer. The first upper main electrode part and the second lower sub electrode part are connected. The first upper sub electrode part and the second lower main electrode part are connected. The first lower electrode layer and the second upper electrode layer are connected.

6 Claims, 8 Drawing Sheets

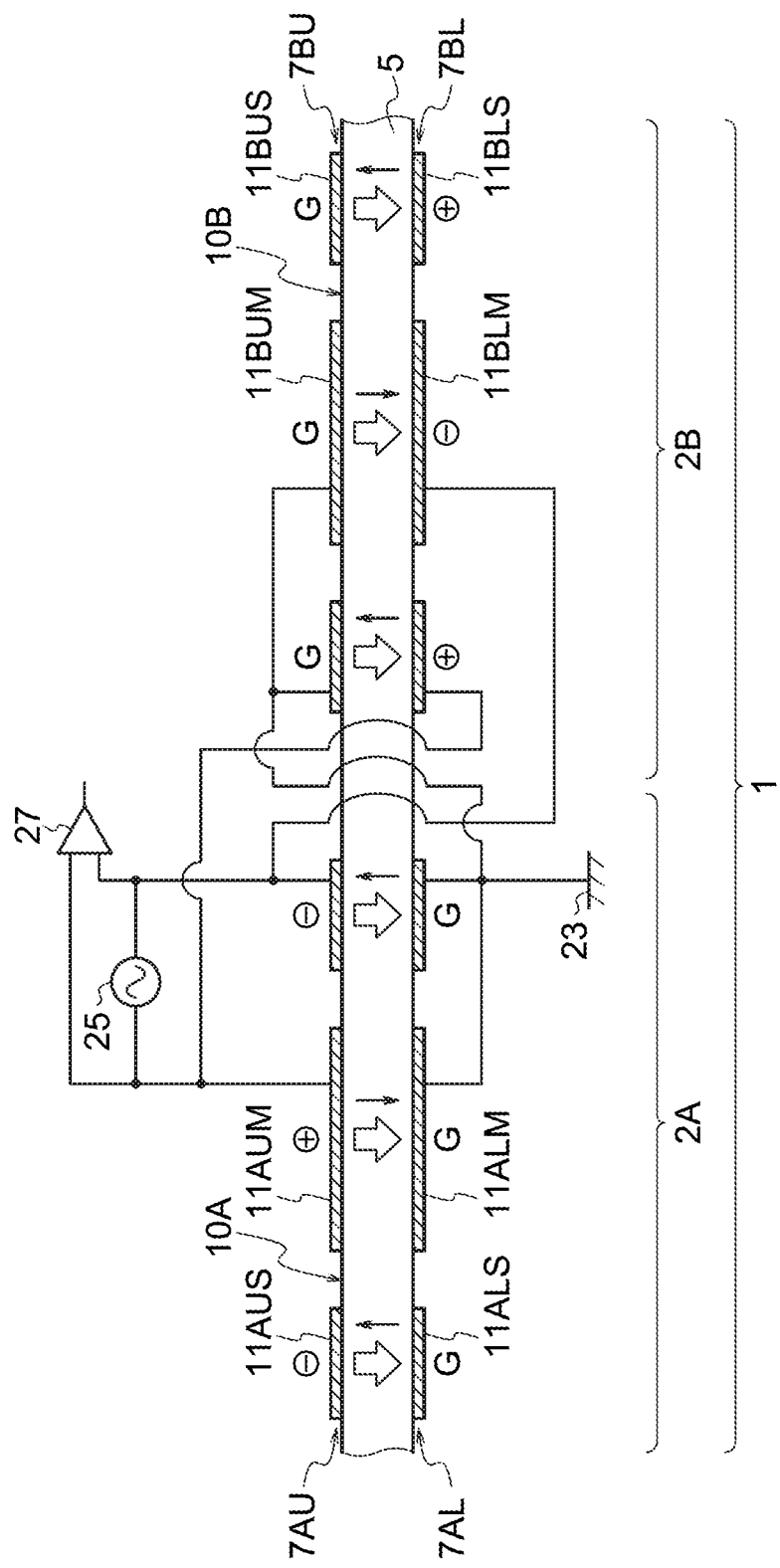

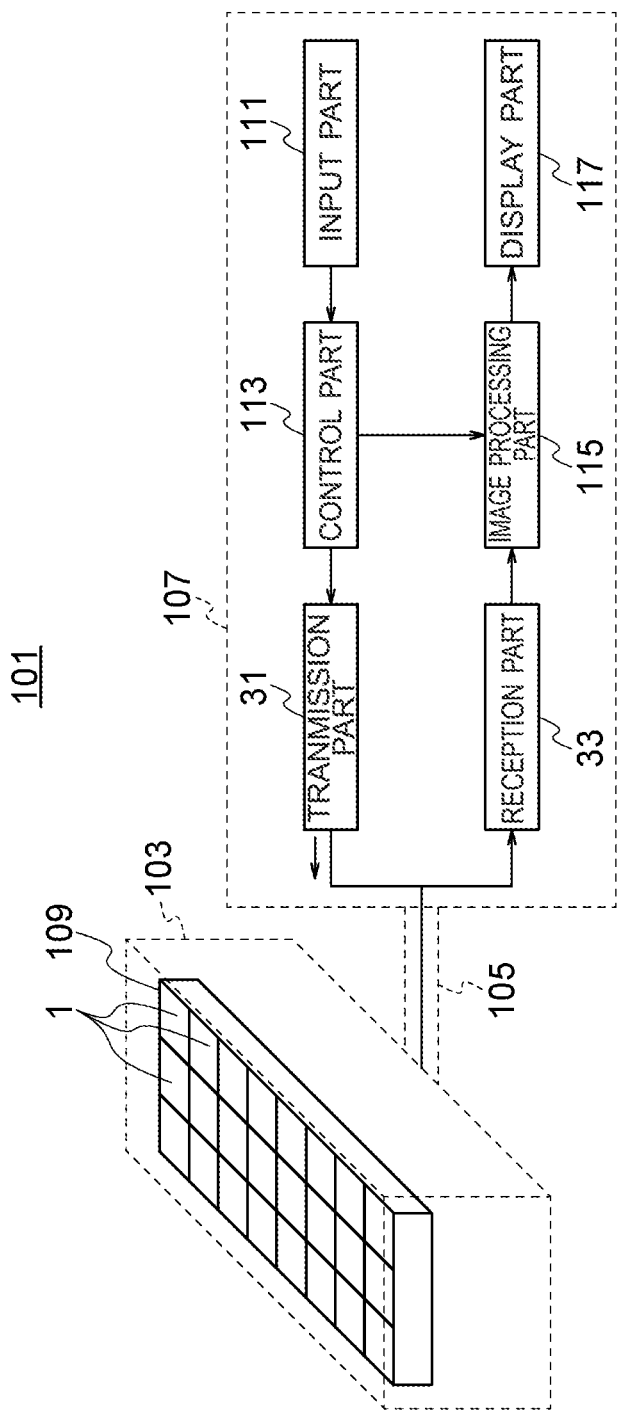

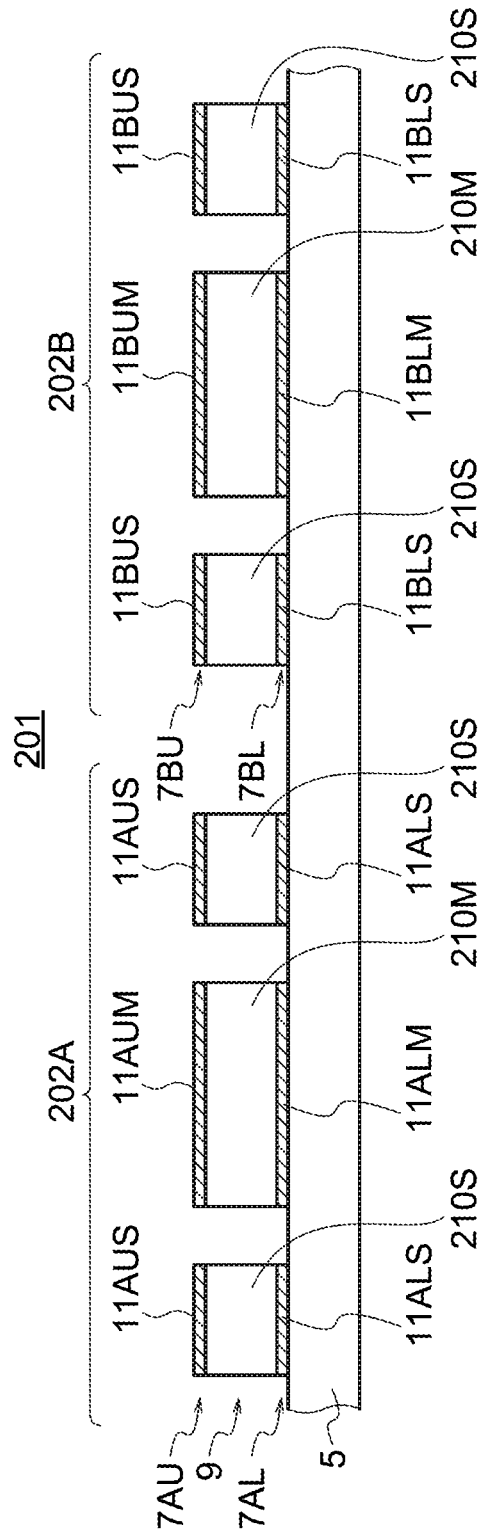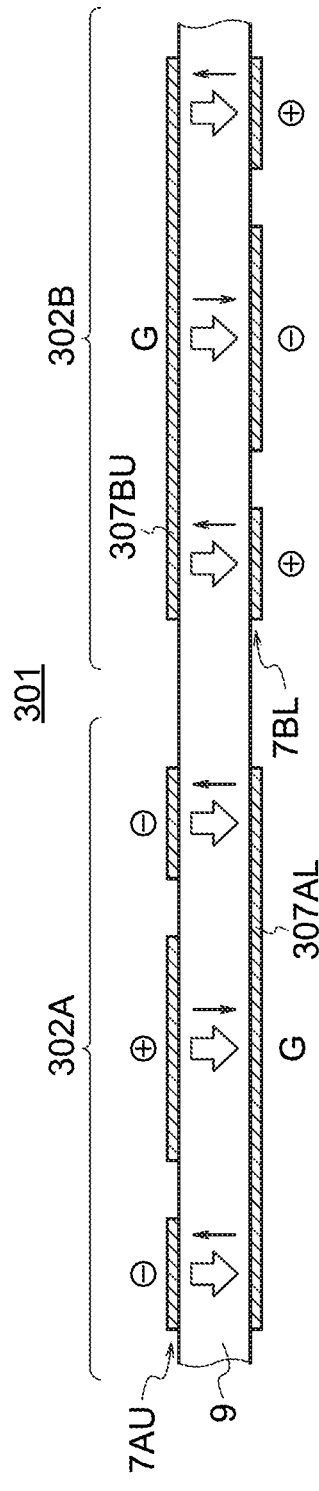

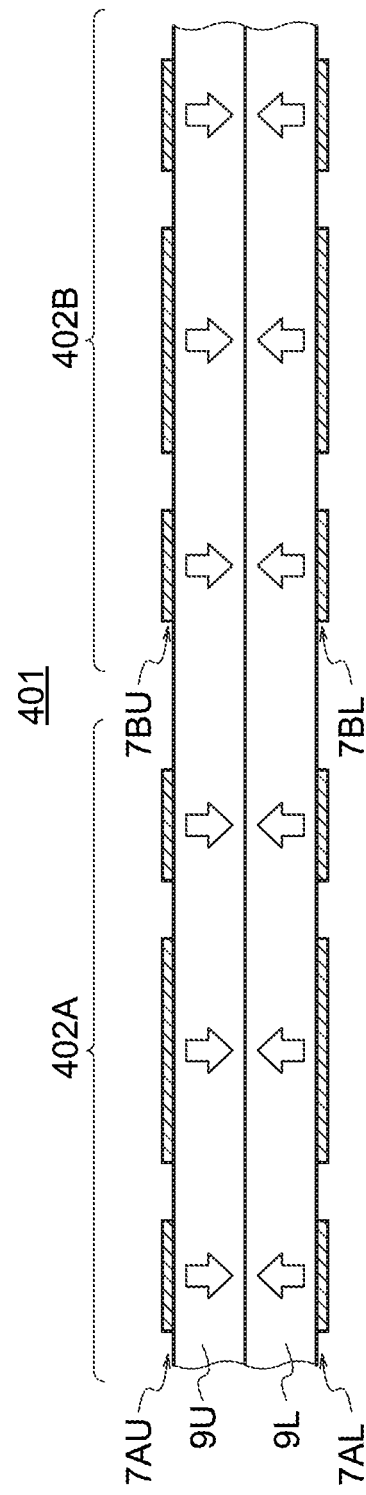
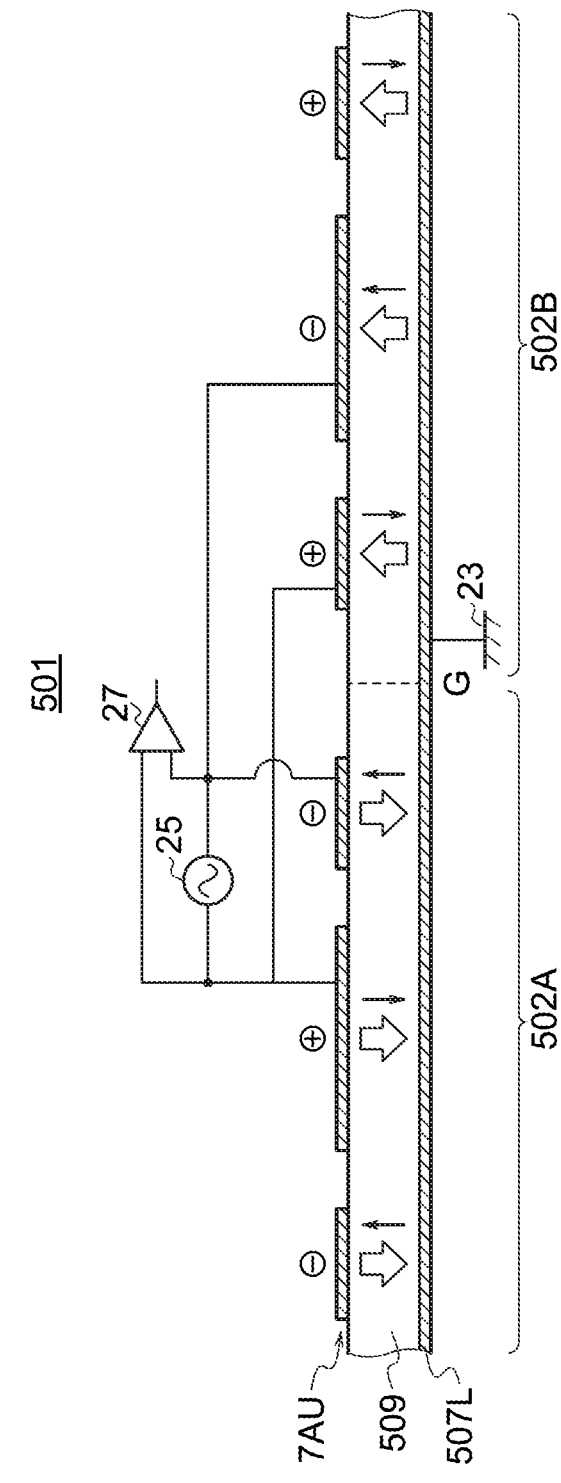

ULTRASONIC SENSOR AND ULTRASONIC SENSOR DEVICE

TECHNICAL FIELD

The present disclosure relates to a pMUT (piezoelectric micromachined ultrasonic transducer) or another piezoelectric type ultrasonic sensor and an ultrasonic sensor device including the ultrasonic sensor.

BACKGROUND ART

As an ultrasonic sensor utilized for an ultrasonic probe of an ultrasonic diagnosis device etc., there is known one using a piezoelectric film (Patent Literature 1). For example, an ultrasonic sensor has a membrane, lower electrode, piezoelectric film, and upper electrode laid in that order above a cavity. In the piezoelectric film, the thickness direction is made the direction of polarization (direction of spontaneous polarization).

When voltage is applied to a piezoelectric film in its thickness direction, the piezoelectric film expands and contracts in its planar direction. This expansion and contraction is restricted by the membrane. Accordingly, the multilayer member including the membrane and piezoelectric film flexurally deforms in the overlaid direction like a bimetal. In turn, a pressure wave is formed in the atmosphere around the multilayer member. Further, when electrical signals changing in voltages with suitable waveforms are input to a lower electrode and upper electrode, ultrasound reflecting the waveforms of those electrical signals (for example reflecting the frequencies) is transmitted. Further, by an action reverse to that described above, the ultrasound received by the multilayer member is converted to an electrical signal reflecting the waveform of that ultrasound.

Patent Literature 1 discloses an ultrasonic sensor which, when viewed on a plane, has a first piezoelectric film positioned at the center area of a cavity, a second piezoelectric film positioned on an outer periphery of the cavity, a first electrode positioned on the piezoelectric film, and a second electrode positioned on the second piezoelectric film and in which the first electrode and the second electrode are not connected.

CITATION LIST

Patent Literature

Patent Literature 1: Japanese Patent Publication No. 2013-135793

SUMMARY OF INVENTION

An ultrasonic sensor according to one aspect of the present disclosure includes a piezoelectric layer, a first element part, and a second element part. The piezoelectric layer includes a first region and a second region which face cavities different from each other and each has a thickness direction as a direction of polarization. The first element part includes the first region. The second element part includes the second region. The first element part includes a first upper electrode layer which is located on one side among a positive side and negative side in the direction of polarization relative to the first region and a first lower electrode layer which is located on the other side among the positive side and negative side in the direction of polarization relative to the first region. The second element part includes a second upper electrode layer which is located on the one side among the positive side and negative side in the direction of polarization relative to the second region and a second lower electrode layer which is located on the other side among the positive side and negative side in the direction of polarization relative to the second region. The first upper electrode layer, when viewed on a plane, includes a first upper main electrode part including a part located on a center side in the first region and a first upper sub electrode part including a part located at an outer side of the first region from the first upper main electrode part. The second lower electrode layer, when viewed on a plane, includes a second lower main electrode part including a part located on a center side in the second region and a second lower sub electrode part including a part located at an outer side of the second region from the second lower main electrode part. A planar shape of an overlapping region of the first upper main electrode part and a first lower electrode layer and a planar shape of an overlapping region of the second lower main electrode part and the second upper electrode layer are the same. A planar shape of an overlapping region of the first upper sub electrode part and the first lower electrode layer and a planar shape of an overlapping region of the second lower sub electrode part and the second upper electrode layer are the same. The first upper main electrode part and the second lower sub electrode part are connected. The first upper sub electrode part and the second lower main electrode part are connected. The first lower electrode layer and the second upper electrode layer are connected.

An ultrasonic sensor device according to one aspect of the present disclosure includes an ultrasonic sensor, a reference potential part, a driving part, and a detection part. The reference potential part, the driving part, and the detection part are connected to the ultrasonic sensor. The ultrasonic sensor includes a piezoelectric layer, a first element part, and a second element part. The piezoelectric layer includes a first region and a second region which face cavities different from each other and each has a thickness direction as a direction of polarization. The first element part includes the first region. The second element part includes the second region. The first element part includes a first upper electrode layer which is located on one side among a positive side and negative side in the direction of polarization relative to the first region and a first lower electrode layer which is located on the other side among the positive side and negative side in the direction of polarization relative to the first region. The second element part includes a second upper electrode layer which is located on the one side among the positive side and negative side in the direction of polarization relative to the second region and a second lower electrode layer which is located on the other side among the positive side and negative side in the direction of polarization relative to the second region. The first upper electrode layer, when viewed on a plane, includes a first upper main electrode part including a part located on a center side in the first region and a first upper sub electrode part including a part located at an outer side of the first region from the first upper main electrode part. The second lower electrode layer, when viewed on a plane, includes a second lower main electrode part including a part located on a center side in the second region and a second lower sub electrode part including a part located at an outer side of the second region from the second lower main electrode part. A planar shape of an overlapping region of the first upper main electrode part and a first lower electrode layer and a planar shape of an overlapping region of the second lower main electrode part and the second upper electrode layer are the same. A planar shape of an overlapping region of the first upper sub electrode part and the first lower electrode layer and a planar shape of an overlapping region of the second lower sub electrode part and the second upper electrode layer are the same. The reference potential part is connected to the first lower electrode layer and the second upper electrode layer. The driving part can give potentials having inverse polarities to each other to a group of electrodes including the first upper main electrode part and the second lower sub electrode part and a group of electrodes including the first upper sub electrode part and the second lower main electrode part. The detection part can detect an electrical signal generated between the two groups of electrodes.

BRIEF DESCRIPTION OF DRAWINGS

FIG. 3 is a schematic cross-sectional view showing the configuration of a principal part of the ultrasonic sensor.

FIG. 5 is a block diagram schematically showing the configuration of an ultrasonic diagnosis device as an example of application of the ultrasonic sensor.

FIG. 6A and FIG. 6B are schematic cross-sectional views showing the configurations of sensors according to one modification and another modification.

FIG. 7A and FIG. 7B are schematic cross-sectional views showing the configurations of sensors according to one modification and another modification

DESCRIPTION OF EMBODIMENTS

Below, an embodiment according to the present disclosure will be explained with reference to the drawings. Note that, the following drawings are schematic ones. Therefore, details will be sometimes omitted. Further, size ratios etc. do not always coincide with the actual ones. Further, size ratios among the plurality of drawings do not always coincide with each other.

The drawings, for convenience, will sometimes have an orthogonal coordinate system D1-D2-D3 attached. Note that, in the sensor, any direction may be defined as "above" or "below". In the explanation of the embodiments, however, sometimes the "upper part" or "lower part" and other terms will be used where the positive side in the D3 axis direction is the upper part. Further, when referred to as "viewed on a plane" in the following description, it means "viewed in the D3 axis direction" unless particularly explained otherwise.

(Configuration of Element Part)

Figure 1A:
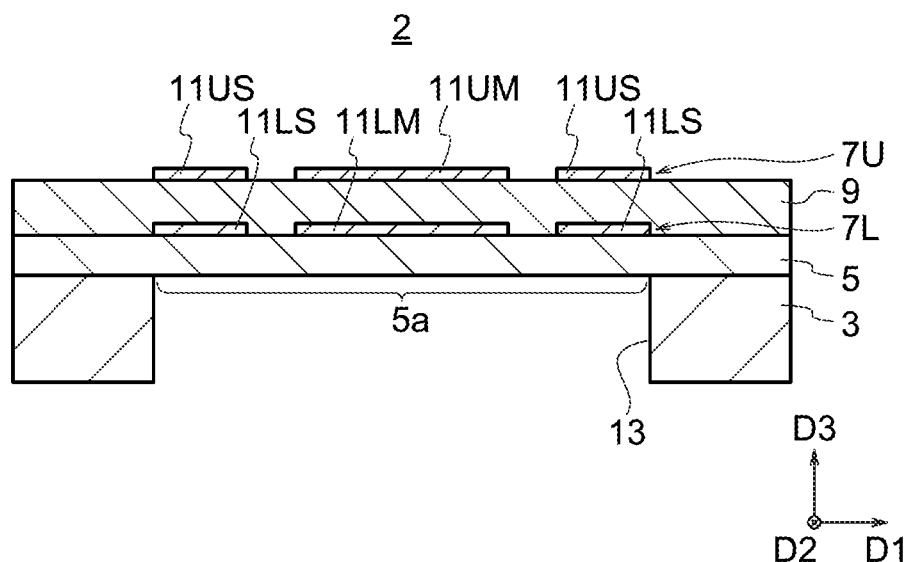
FIG. 1A is a cross-sectional view showing the configuration of an element part in an ultrasonic sensor according to an embodiment.
Figure 1B:
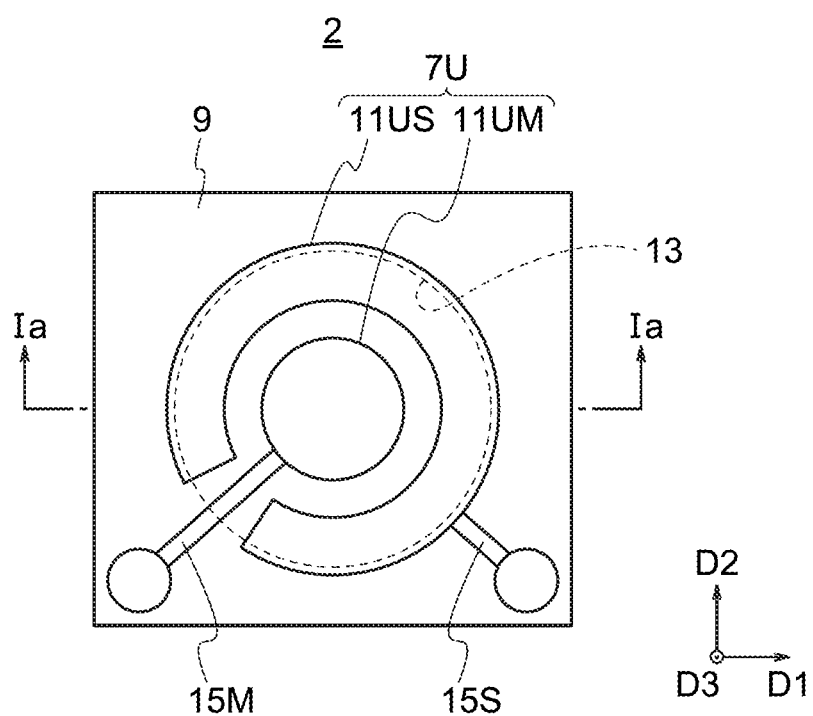
FIG. 1B is a plan view of the element part in FIG. 1A.

FIG. 1A is a cross-sectional view showing the configuration of an element part 2 included in an ultrasonic type sensor 1 (FIG. 3) according to an embodiment, and FIG. 1B is a plan view showing the configuration of the element part 2. Note that, FIG. 1A corresponds to the Ia-Ia line in FIG. 1B.

The sensor 1, for example, as will be explained later, has two element parts 2. In FIG. 1A and FIG. 1B, only one element part 2 is shown. The element part 2 is for example configured as a pMUT. The element part 2, for example, receives as input an electrical signal changing in voltage with a predetermined waveform (for example rectangular wave or sine wave). Further, the element part 2 converts that electrical signal to an ultrasound reflecting the waveform of the electrical signal (for example reflecting the frequency) and transmits the result to one among the positive side and negative side in the D3 axis direction. Further, for example, the element part 2 receives the ultrasound from the one among the positive side and negative side in the D3 axis direction and converts that ultrasound to an electrical signal reflecting the waveform of the ultrasound.

Note that, the positive side or negative side in the D3 axis direction for transmission and reception of the ultrasound referred to here is not always parallel to the D3 axis direction. Further, the frequency band of the ultrasound is for example a frequency band of 20 kHz or more. The upper limit of the frequency of the ultrasound is not particularly restricted. However, for example, the upper limit is 5 GHz.

The element part 2, for example, as shown in FIG. 1A, has a base body 3, membrane 5, lower electrode layer 7L, piezoelectric layer 9, and upper electrode layer 7U which are overlaid in that order from the lower part. Note that, sometimes the lower electrode layer 7L and upper electrode layer 7U will be simply referred to as the "electrode layers 7" and will not be differentiated.

The base body 3 for example has a cavity 13. The various members (5, 7, 9, etc.) above the base body 3 configure a vibration region part vibrating for transmission and reception of ultrasound by the parts positioned above the cavity 13. The vibration region part, for vibration of a primary mode of flexural deformation which will be explained later, may be configured so that the resonance frequency is positioned in the frequency band of the ultrasound.

The cavity 13 may be a concave shaped one which opens upward in the base body 3 or a via hole-shaped one passing through the base body 3. The planar shape and dimensions of the cavity 13 may be suitably set. In the example shown, the planar shape of the cavity 13 is circular. Further, the planar shape is constant in the depth direction (D3 axis direction) of the cavity 13.

Note that, unlike the example shown, the planar shape of the cavity 13 need not be constant in the depth direction of the cavity 13. For example, the cavity 13 may become smaller in diameter toward the upper surface side as well. When considering such an aspect, in the explanation of the present embodiment etc., the term of the "planar shape of the cavity 13" may be grasped as designating the planar shape of the upper surface of the cavity 13. This is because, mainly, it is the upper surface of the cavity 13 that restricts the region of the membrane 5 etc. which can vibrate.

The material of the base body 3 may be any material. Further, the base body 3 may be integrally formed or may be formed by a combination of a plurality of members. For example, the material for the base body 3 is an inorganic insulating material or organic insulating material. More specifically, for example, the base body 3 may be integrally formed by silicon (Si) or another insulating material. Further, for example, the base body 3 may be integrally formed in substantially its entirety by silicon or another insulating material and may have a layer made of $SiO_2$ or another insulating material on its upper surface.

The membrane 5 is for example layer shaped having a constant thickness and covers the cavity 13. The area of the membrane 5 is broader than the area of the cavity 13. The membrane 5 is fixed to the base body 3 on the periphery of the cavity 13 to be supported there. Note that, in the membrane 5, a region overlaying the cavity 13 will be sometimes referred to as a "vibration part 5*a*". The thickness of the membrane 5 may be suitably set.

The membrane 5 is for example formed by an insulating material. The insulating material may be an inorganic material or organic material. More specifically, for example, it is silicon, silicon oxide ($SiO_2$), or silicon nitride (SiN). Note that, the membrane 5 may be configured by overlaying a plurality of layers which are made of different materials from each other as well. Further, the membrane 5 may be made of the same material as that for the base body 3 and integrally formed with the base body 3.

The piezoelectric layer 9 is for example basically layer shaped having a constant thickness and has a size schematically the same as that of the membrane 5. Note that, in the example shown, in the piezoelectric layer 9, a region overlapping the lower electrode layer 7L becomes thinner by the amount of the thickness of the lower electrode layer 7L relative to the region which does not overlap the lower electrode layer 7L. In the explanation which will be given later, sometimes the change of the thickness will be omitted. In the piezoelectric layer 9, the direction of polarization is made the thickness direction. Further, the orientation of polarization (direction of positive or negative) and strength are substantially constant over the entirety of the piezoelectric layer 9.

The material for the piezoelectric layer 9 only have to be a piezoelectric substance. For example, it is aluminum nitride (AlN), barium titanate (BTO: $BaTiO_3$), potassium sodium niobite (KNN: $(K,Na)NbO_3$), sodium bismuth titanate (NBT: $Na_{0.5}Bi_{0.5}TiO_3$), or lead zirconate titanate (PZT: $Pb(Zr_x, Ti_{1-x})O_3$). As understood also from the above illustration, the piezoelectric substance may be or may not be a ferroelectric substance and may be or may not be a pyroelectric substance. Further, the crystal structure may be a suitable one such as the perovskite type or wurtzite type.

The lower electrode layer 7L has a lower main electrode part 11LM and lower sub electrode part 11LS having mutually different planar shapes at mutually different positions in the planar direction. In the same way, the upper electrode layer 7U has an upper main electrode part 11UM and upper sub electrode part 11US having mutually different planar shapes at mutually different positions in the planar direction.

Note that, in the following explanation, sometimes the lower main electrode part 11LM and upper main electrode part 11UM will be simply referred to as the "main electrode parts 11M" and will not be differentiated. Further, sometimes the lower sub electrode part 11LS and upper sub electrode part 11US will be simply referred to as the "sub electrode parts 11S" and will not be differentiated. Further, sometimes the main electrode part 11M and the sub electrode part 11S will not be differentiated and will be simply referred to as the "electrode parts 11".

The lower main electrode part 11LM and the upper main electrode part 11UM for example have the same planar shapes as each other and face each other. Accordingly, the planar shape of the overlapping region of the same (region where they overlap each other when viewed on a plane) is the same as the planar shapes of the individual main electrode parts 11M. In the same way, the lower sub electrode part 11LS and the upper sub electrode part 11US for example have the same planar shapes as each other and face each other. Accordingly, the planar shape of the overlapping region of them is the same as the planar shapes of the individual sub electrode parts 11S.

The main electrode parts 11M, for example, include parts which are positioned at the center and/or on the center side of the cavity 13 when viewed on a plane. Note that, the center of the cavity 13 when viewed on a plane is for example the center of gravity of the figure. The center of gravity of the figure is a point where the primary moment around that is 0. In the example shown, the planar shape of the cavity 13 is circular, therefore the center of gravity of the figure is the center of the circle. The center side is for example the side closer to the center than an intermediate position between the center and the outer edge of the cavity 13. Further, the main electrode parts 11M, when viewed on a plane, are smaller than the cavity 13 and fit into the cavity 13.

The planar shapes of the main electrode parts 11M are for example made substantially the same as the planar shape of the cavity 13 and/or have outer edges having substantially constant distances from the outer edge of the cavity 13. In the example shown, the planar shape of the cavity 13 is circular, therefore the main electrode parts 11M are circular shaped concentrically with the cavity 13 and having smaller diameters than the cavity 13.

The sub electrode parts 11S, for example, when viewed on a plane, include parts which are positioned at the outer side of the cavity 13 from the main electrode parts 11M. More specifically, for example, the sub electrode parts 11S have shapes that surround the main electrode parts 11M when viewed on a plane. When referring to as "surround the main electrode parts 11M", for example, when considering the ranges of angle around the centers of gravity of the figures of the main electrode parts 11M, the sums of the ranges of angle in which the sub electrode parts 11S exist may exceed 180° and/or the largest ranges of angle in which the sub electrode parts 11S do not exist may be less than 120°.

In the example shown, the sub electrode parts 11S extend over ranges exceeding a semicircle (180°) so as to surround the main electrode parts 11M, and satisfy both of the two conditions described above. More specifically, for example, the sub electrode parts 11S extend over ranges exceeding 270° with constant widths. The shapes thereof are made substantially the same as the outer edges of the main electrode parts 11M (and/or cavity 13) and/or have inner edges and outer edges having substantially constant distances from the outer edges of the main electrode parts 11M (and/or cavity 13). In the example shown, the shapes of the sub electrode parts 11S are arc shapes.

The sub electrode parts 11S for example substantially fit in the cavity 13 when viewed on a plane. In other words, the sub electrode parts 11S have regions overlapping the cavity 13 when viewed on a plane. The areas of the overlapping regions are larger than the areas (substantially 0 in the example shown) of the regions which do not overlap it. Further, from another viewpoint, in the example shown, the sub electrode parts 11S substantially match in outer edges with the outer edge of the cavity 13.

The electrode parts 11 are for example layer shaped having constant thicknesses. The thickness may be suitably set. The material for the electrode parts 11 may be a suitable metal. For example, it is gold (Au), platinum (Pt), aluminum (Al), copper (Cu), or chromium (Cr). The electrode parts 11 may be configured by stacking a plurality of layers made of mutually different materials as well.

In each of the electrode layers 7, the materials and thicknesses of the main electrode part 11M and the sub electrode part 11S are for example the same as each other.

However, in each of the electrode layers 7, the materials and/or thicknesses of the main electrode part 11M and the sub electrode part 11S may be mutually different as well. Further, between the two electrode layers 7, the materials and thicknesses of the main electrode parts 11M are for example the same as each other. In the same way, between the two electrode layers 7, the materials and thicknesses of the sub electrode parts 11S are for example the same as each other. However, between the two electrode layers 7, the materials and/or thicknesses of the main electrode parts 11M and/or sub electrode parts 11S may be mutually different as well.

The element part 2 may have suitable connection conductors as well for input of signals (voltages) to the lower electrode layer 7L and upper electrode layer 7U and output of the signals (for example voltages) from these electrode layers.

In FIG. 1B, connection conductors 15M and 15S (below, sometimes S and M will be omitted) connected to the upper electrode layer 7U are illustrated. The connection conductors 15, for example, are formed by layer-shaped conductors which are provided on the piezoelectric layer 9. The front ends of the connection conductors 15 are for example connected to not shown via conductors which pass through the piezoelectric layer 9, membrane 5, and base body 3 (at least a part of the base body 3). The input and output of signals to/from the electrode parts 11 in the upper electrode layer 7U are carried out through these via conductors.

For the lower electrode layer 7L, for example, although particularly not shown, connection conductors 15 configured by layer-shaped conductors are provided between the membrane 5 and the piezoelectric layer 9. These connection conductors 15 are for example connected to not shown via conductors passing through the membrane 5 and the base body 3 (at least a part of the base body 3). Through these via conductors, input and output of signals are carried out with respect to the electrode parts 11 in the lower electrode layer 7L.

The planar shapes of the connection conductors 15 shown in FIG. 1B are examples of a case where the main electrode parts 11M and the sub electrode parts 11S are not connected. The connection conductors 15M are led out of the main electrode parts 11M. The connection conductors 15S are led out of the sub electrode parts 11S. The sub electrode parts 11S are partially cut. The connection conductors 15M extend from the inside to the outside of the sub electrode parts 11S through the cut parts.

In a case where the main electrode part 11M and the sub electrode part 11S are rendered the same potential, for example, although not particularly shown, connection conductor 15 connecting the main electrode part 11M and the sub electrode part 11S and connection conductor 15S the same as those in FIG. 1B may be provided. In this case, cutting of the sub electrode part 11S is unnecessary.

As will be understood from the explanation which will be given later, in either of the lower electrode layer 7L or upper electrode layer 7U, cutting of the sub electrode part 11S is unnecessary. The planar shapes of the lower electrode layer 7L and the upper electrode layer 7U may be different from each other only by the amount of the cut or a cut part may be formed even in the electrode layer 7 which need not be cut to make their shapes the same as each other.

In the explanation of the present disclosure, when referring to the "planar shapes are the same as each other with respect to the electrode layers 7 or electrode parts 11", the difference caused due to the arrangement of the connection conductors 15 as described above (influence of any cuts) will be ignored. Note that, naturally tolerances or allowable differences may be ignored.

(Driving Part, Detection Part, and Reference Potential Part)

Figure 2A:
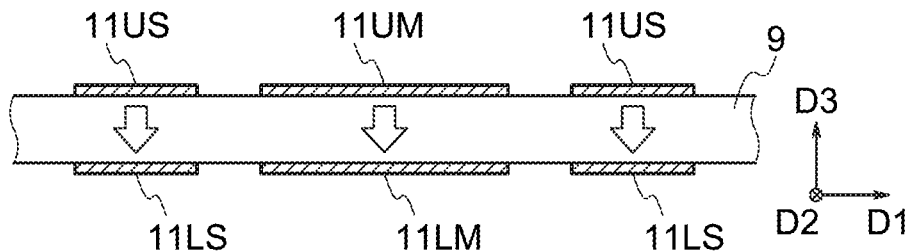
FIG. 2A, FIG. 2B, FIG. 2C, and FIG. 2D are schematic cross-sectional views for explaining the mode of operation of the element part.
Figure 2B:
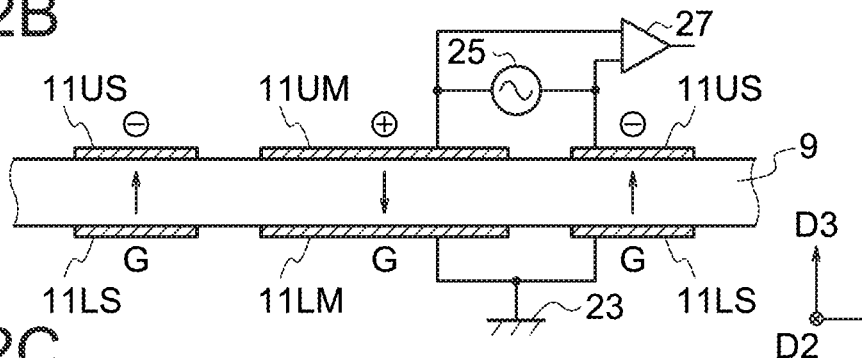

FIG. 2B is a cross-sectional view (hatching showing cross-section suitably omitted) schematically showing the element part 2 (piezoelectric layer 9 and electrode layers 7), a reference potential part 23 which gives the reference potential to the element part 2, a driving part 25 which inputs electrical signals to the element part 2, and a detection part 27 which detects the electrical signals from the element part 2.

The arrows in the piezoelectric layer 9 indicate the directions of the voltages at a predetermined point of time. "+", "−", and "G" attached to the electrode parts 11 indicate, at the above point of time, that the potentials are positive, negative, and the reference potential.

The reference potential part 23 is a part given a potential which becomes the reference of the electrical circuit. For example, it may be a part of the driving part 25 and/or detection part 27, may be configured by only a conductor on a circuit board, or may be configured including a housing. The reference potential part 23 is connected to the main electrode part 11M and sub electrode part 11S in one of the two electrode layers 7 (lower electrode layer 7L in the example shown).

The driving part 25, as indicated by the notation showing a power supply for convenience, for example, is configured including a power supply circuit which converts a commercial power supply to a signal of a voltage having a suitable waveform and outputs the result. The driving part 25 is connected to the main electrode part 11M and sub electrode part 11S in the other (upper electrode layer 7U in the example shown) between the two electrode layers 7 and supplies voltages (inputs electrical signals) to these electrode parts 11 so as to give potentials being inverse in polarity (positive and negative relative to the reference potential) to each other to them.

The reference potential part 23 and driving part 25 are connected in this way, therefore, in the piezoelectric layer 9, a part between the two main electrode parts 11M and a part between the two sub electrode parts 11S are supplied with voltages having inverse orientations to each other. Note that, in the example shown, a downward voltage is supplied between the two main electrode parts 11M, and an upward voltage is supplied between the two sub electrode parts 11S. However, voltages being inverse to the above with respect to relationships between the electrode parts 11 and orientations of the voltages may be supplied them as well.

The detection part 27, as indicated by the notation showing an amplifier for convenience, for example, is configured including an amplifier which amplifies the input electrical signal and outputs the result. The amplifier may be for example a charge amplifier or may be a voltage amplifier. That is, the electrical signal detected by the detection part 27 may be one based on a charge, may be one based on a potential difference, or may be another one based on a physical quantity which is equivalent or correlated to them. Note that, the workload when carrying the charges is the potential difference, therefore the detection of the charge and the detection of the potential difference (voltage) may be equivalent. In the explanation of the present embodiment, sometimes an explanation will be given by taking as an example only one of these equivalent or correlated physical quantities.

The detection part 27, in the same way as the driving part 25, is connected to the main electrode part 11M and sub electrode part 11S in the other of the two electrode layers 7 (upper electrode layer 7U in the example shown) and can detect the electrical signal generated between them. Specifically, for example, the detection part 27 can detect the charge between the two electrode parts. Further, for example, the detection part 27 can detect the potential difference between the two electrode parts.

(Mode of Operation of Element Part)

FIG. 2A to FIG. 2D are schematic cross-sectional views (hatchings showing cross-sections suitably omitted) for explaining the mode of operation of the sensor.

In FIG. 2A, the white arrows in the piezoelectric layer 9 indicate the direction of polarization. As already explained, in the piezoelectric layer 9, the thickness direction (D3 axis direction) is made the direction of polarization. Further, the orientation and intensity of polarization are constant over the entirety of the piezoelectric layer 9. Note that, in the example shown, the orientation of polarization is downward. However, naturally it may be upward as well.

In FIG. 2B, the black arrows in the piezoelectric layer 9 indicate the directions of voltages (electric fields). As understood from a comparison between FIG. 2A and FIG. 2B, in the example shown, the piezoelectric layer 9 is supplied with voltage with the same orientation as the orientation of polarization by the main electrode parts 11M and is supplied with voltage with an inverse orientation to the orientation of polarization by the sub electrode parts 11S.

Figure 2C:
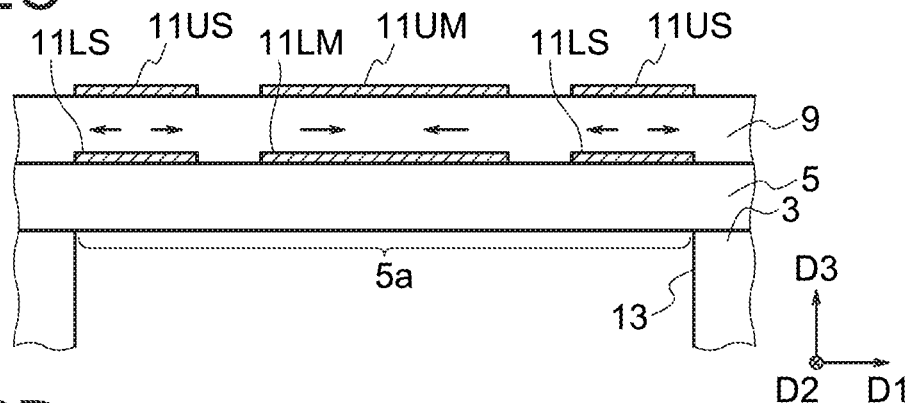

In FIG. 2C, the arrows in the piezoelectric layer 9 indicate the directions of expansion and contraction due to the piezoelectric transverse effect. As a result of application of the voltages as described above, the piezoelectric layer 9 tries to contract in the planar direction (D1 axis direction and D2 axis direction) in the region overlapping the main electrode parts 11M while trying to expand in the planar direction in the region overlapping the sub electrode parts 11S.

Figure 2D:
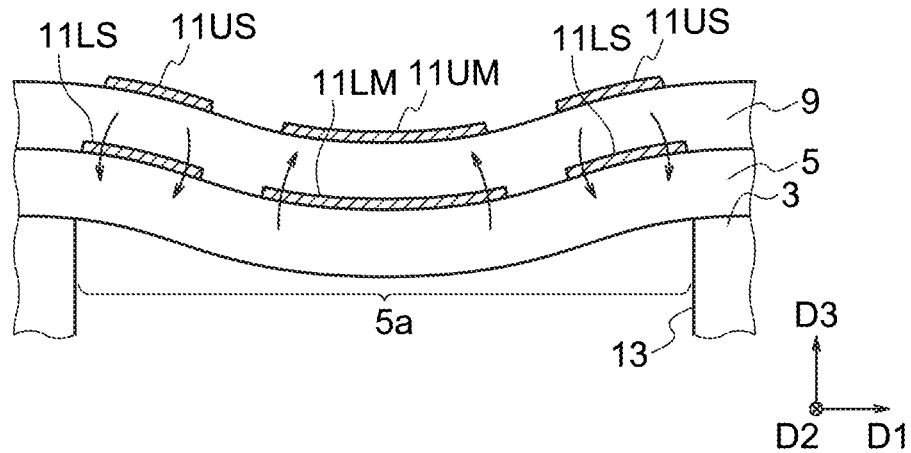

In FIG. 2D, the arrows in the piezoelectric layer 9 and membrane 5 indicate directions of bending moments. The piezoelectric layer 9 tries to contract or expand as described above, while the deformation thereof is restricted by the membrane 5. As a result, the vibration part 5a and the piezoelectric layer 9 flex to the cavity 13 side like a bimetal in the region overlapping the main electrode parts 11M. On the other hand, the vibration part 5a and piezoelectric layer 9 flex to the side opposite to the cavity 13 like a bimetal in the regions overlapping the sub electrode parts 11S. Further, the vibration part 5a as a whole flexes to the cavity 13 side.

In the above description, the explanation was given by taking as an example the case where the vibration part 5a flexes to the cavity 13 side. Conversely to the above description, if voltage is supplied to the piezoelectric layer 9 in an inverse orientation to the orientation of polarization by the main electrode parts 11M and voltage is supplied in the same orientation as the orientation of polarization by the sub electrode parts 11S, according to the same principle, the vibration part 5a displaces to the side opposite to the cavity 13.

Due to the displacement of the vibration part 5a described above, a pressure wave is formed in the atmosphere around the vibration part 5a. Further, due to an electrical signal changing in voltage with a predetermined waveform being input to one electrode layer (upper electrode layer 7U in the example shown), an ultrasound reflecting the waveform (for example frequency) of that electrical signal is generated.

Note that, the electrical signal for example may be one by which application of voltage making the vibration part 5a displace to the cavity 13 side and application of voltage making the vibration part 5a displace to the side opposite to the cavity 13 are repeated. That is, the electrical signal may be one by which the polarity (positive and negative) of the voltage is inverted along with the elapse of time (the orientations of the voltages (electric fields) are alternately replaced by each other in the D3 axis direction).

Further, for example, the electrical signal may be one by which only application of voltage making the vibration part 5a displace to the cavity 13 side or only application of voltage making the vibration part 5a displace to the side opposite to the cavity 13 is repeated. In this case, the ultrasound is generated by repetition of flexing and cancellation of flexing by a restoring force.

Further, the waveform of the electrical signal may be a suitable one. For example, in one ultrasonic signal (echo signal), the number of waves may be suitably set, and the frequency and voltage may be constant or may not be constant. In the case where the polarity of the electrical signal changes, the voltage on the positive side and the voltage on the negative side may have the same magnitude or have different magnitudes.

The transmission of the ultrasound was explained. The reception of the ultrasound is realized according to an inverse principle to that at the time of transmission. The element part 2 for example intermittently transmits the ultrasonic signal and receives the ultrasonic signal the periods where the ultrasonic signal is not transmitted. Due to this, the element part 2 for example receives the ultrasonic signal which was transmitted by itself, reflected, and returned.

(Configuration of Sensor)

FIG. 3 is a schematic cross-sectional view (hatching showing cross-section suitably omitted) showing the configurations of a sensor 1 including the element part 2 as described above and a sensor device 21 including the sensor 1. Note that, in this view, illustration of the membrane 5 and base body 3 (cavity 13) is omitted. The white arrows and black arrows in the piezoelectric layer 9, in the same way as FIG. 2A and FIG. 2B, indicate the orientations of polarization and directions of the voltages at a predetermined point of time. The meanings of "+", "−", and "G" are the same as those in FIG. 2B.

The sensor 1 has a first element part 2A and second element part 2B. Each of them is the same as the element part 2 explained above Note that, in the following description, sometimes the first element part 2A and second element part 2B will be simply referred to as the "element parts 2" and will not be differentiated. Further, for the parts in the element part 2 already explained, sometimes the term "first" and additional notation "A" will be attached to the configurations concerned with the first element part 2A, and sometimes the term of "second" and additional notation "B" will be attached to the configurations concerned with the second element part 2B.

The two element parts 2 for example basically have the same configuration. For example, the two element parts 2 are provided in a common base body 3, membrane 5, and piezoelectric layer 9. In other words, the base body 3, membrane 5, and piezoelectric layer 9 have sizes covering the two element parts 2. The materials and thicknesses etc. of them are the same between the two element parts 2. As indicated by white arrows in the piezoelectric layer 9, the orientations and strengths of polarizations are the same between the two element parts 2. Further, the planar shape of the cavity 13 and the planar shapes, materials, and thickness etc. of the lower electrode layer 7L and the upper electrode layer 7U are the same between the two element parts 2 (as already explained, the difference due to the connection conductors 15 is ignored).

Further, in the present embodiment, as already explained, in each element part 2, the lower electrode layer 7L and the upper electrode layer 7U are given the same configuration. Accordingly, from another viewpoint, the first lower electrode layer 7AL and the second upper electrode layer 7BU have the same configurations as each other, and the first upper electrode layer 7AU and the second lower electrode layer 7BL have the same configurations as each other. That is, between the two element parts 2, the configurations of the lower electrode layer 7L and the upper electrode layer 7U can be grasped as if they were vertically inverted from each other (including also the parts according to the connection conductors 15 as will be understood from the explanation which will be given later). Note that, between the two element parts 2, the orientations in the planar direction (for example directions in which the sub electrode parts 11S are cut) may be the same as each other, may be inverse to each other, or may be different at suitable angles.

As described above, the piezoelectric layer 9 covers the two element parts 2. In the following description, for convenience, in the piezoelectric layer 9, sometimes the part configuring the first element part 2A will be referred to as the "first region 10A", and the part configuring the second element part 2B will be referred to as the "second region 10B". The first region 10A is a region having the same planar shape as that of the cavity 13 in the first element part 2A, and the second region 10B is a region having the same planar shape as that of the cavity 13 in the second element part 2B. The explanation given above according to the planar shape of the cavity 13 may be grasped as an explanation of the planar shapes of the first region 10A and second region 10B.

(Electrical Connection and Mode of Operation in Sensor)

Between the two element parts 2, the connections with respect to the reference potential part 23, driving part 25, and detection part 27 are inverse with respect to vertical direction, and are inverse with respect to the main electrode parts 11M and the sub electrode parts 11S. From another viewpoint, the two element parts 2 are connected to each other so that the relationships between the potentials in the element parts 11 and upper/lower and inner/outer sides become inverse to each other.

Specifically, in the example shown, the first upper main electrode part 11AUM and the second lower sub electrode part 11BLS are connected, and the first upper sub electrode part 11AUS and the second lower main electrode part 11BLM are connected. Further, the first lower electrode layer 7AL (first lower main electrode part 11ALM and first lower sub electrode part 11ALS), and the second upper electrode part 7BU (second upper main electrode part 11BUM and second upper sub electrode part 11BUS) are connected.

From another viewpoint, the first upper main electrode part 11AUM and the second lower sub electrode part 11BLS are connected to one terminal of the driving part 25 (detection part 27), and the first upper sub electrode part 11AUS and the second lower main electrode part 11BLM are connected to the other terminal of the driving part 25 (detection part 27). Further, the first lower electrode layer 7AL (first lower main electrode part 11ALM and first lower sub electrode part 11ALS) and the second upper electrode layer 7BU (second upper main electrode part 11BUM and second upper sub electrode part 11BUS) are connected to the reference potential part 23.

The connection between the two element parts 2 is for example carried out in the sensor 1. For example, although not particularly shown, the connection may be realized by the connection conductor 15 relating to one element part 2 or the via conductor connected to this connection conductor 15 and the connection conductor 15 relating to the other element part 2 or the via conductor connected to this connection conductor 15 being connected by a layer-shaped wiring pattern in the sensor 1. The wiring pattern may be for example positioned on the piezoelectric layer 9, between the piezoelectric layer 9 and the membrane 5, between the membrane 5 and the base body 3, in the base body 3 and/or on the lower surface of the base body 3. The via conductors connected to the connection conductors 15 may be exposed at the lower surface of the base body 3, and the via conductors may be connected to each other by a flexible board joined to the lower surface of the base body 3.

As a result of connection where the top and bottom and the inside and outside are reversed as described above, for example, when potentials having inverse polarities to each other (positive and negative) are generated at the two terminals in the driving part 25 and voltages are supplied to the two element parts 2, as indicated by the black arrows, the orientations of the voltages become the same between the two element parts 2. Specifically, in the example shown, in the first element parts 2A, a positive potential is given to the first upper main electrode part 11AUM and voltage is supplied in the direction from the top to the bottom (from positive to the reference potential). In the second element part 2B, a negative potential is given to the second lower main electrode part 11BLM and voltage is supplied in the direction from the top to the bottom (from the reference potential to negative potential). Further, in the first element part 2A, a negative potential is given to the first upper sub electrode part 11AUS and voltage is supplied in the direction from the bottom to the top (from the reference potential to the negative potential). In the second element part 2B, a positive potential is given to the second lower sub electrode part 11BLS and voltage is supplied in the direction from the bottom to the top (from positive to the reference potential).

Between the two element parts 2, the orientations of polarization are the same. Further, the orientations of voltages supplied by the driving part 25 are the same. Accordingly, the two element parts 2 are driven so that the vibration parts 5a displace to the same sides as each other in the up-down direction at a predetermined point of time. Further, conversely, when the vibration parts 5a in the two element parts 2 receive the same pressure wave and displace to the same side of the up-down direction, in the two element parts 2, voltages having the same orientations as each other are generated and are input to the detection part 27.

(Method for Manufacturing Sensor)

A method for manufacturing the sensor may be the same as various known manufacturing methods except for the specific shapes of the electrode layers 7, connection conductors 15, and other conductors. For example, a wafer for forming the base body 3 may be repeatedly subjected to a process of formation of a thin film and patterning to form the membrane 5, lower electrode layer 7L, piezoelectric layer 9, and upper electrode layer 7U. Note that, formation of the thin film and patterning may be separately carried out or may be simultaneously carried out by formation of a thin film through a mask.

As described above, in the present embodiment, the sensor 1 has a piezoelectric layer 9 including a first region 10A (FIG. 3) and second region 10B (FIG. 3) which face cavities which are different from each other and have the thickness directions as directions of polarization, a first element part 2A including the first region 10A, and a second element part 2B including the second region 10B. Each element part 2 has an upper electrode layer 7U overlapping one side (negative side in the example in FIG. 3) among the positive side and negative side in the direction of polarization and a lower electrode layer 7L overlapping the other side among the positive side and negative side in the direction of polarization.

A first upper electrode layer 7AU, when viewed on a plane, has a first upper main electrode part 11AUM including a part positioned on a center side in the first region 10A and a first upper sub electrode part 11AUS including a part positioned at an outer side of the first region 10A from the first upper main electrode part 11AUM. A second lower electrode layer 7BL, when viewed on a plane, has a second lower main electrode part 11BLM including a part positioned on a center side in the second region 10B and a second lower sub electrode part 11BLS including a part positioned at an outer side of the second region 10B from the second lower main electrode part 11BLM. The planar shape of the overlapping region of the first upper main electrode part 11AUM and the first lower electrode layer 7AL and the planar shape of the overlapping region of the second lower main electrode part 11BLM and the second upper electrode layer 7BU are the same. The planar shape of the overlapping region of the first upper sub electrode part 11AUS and the first lower electrode layer 7AL and the planar shape of the overlapping region of the second lower sub electrode part 11BLS and the second upper electrode layer 7BU are the same. The first upper main electrode part 11AUM and the second lower sub electrode part 11BLS are connected. The first upper sub electrode part 11AUS and the second lower main electrode part 11BLM are connected. The first lower electrode layer 7AL and the second upper electrode layer 7BU are connected.

Further, from another viewpoint, the sensor device 21 has a sensor 1 as described above, a reference potential part 23, a driving part 25, and a detection part 27. The reference potential part 23 is connected to the first lower electrode layer 7AL and second upper electrode layer 7BU. The driving part 25 gives potentials having inverse polarities to each other to the group of electrodes including the first upper main electrode part 11AUM and second lower sub electrode part 11BLS and the group of electrodes including the first upper sub electrode part 11AUS and second lower main electrode part 11BLM. The detection part 27 detects the electrical signal (for example charge or potential difference) generated between the above two groups of electrodes.

Accordingly, for example, the SN ratio in the sensor 1 can be improved. Specifically, this is as follows.

Figure 4A:
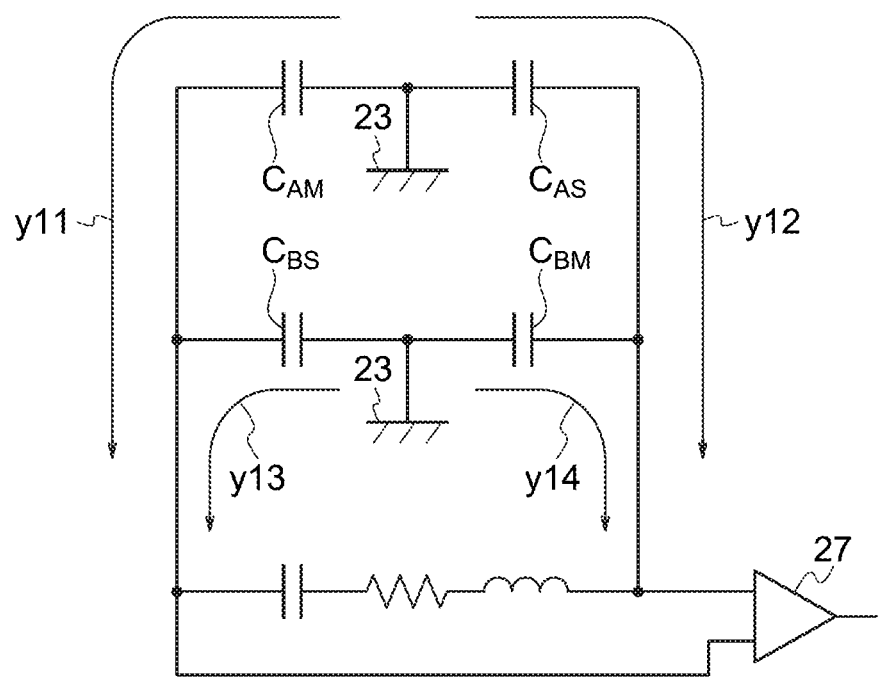
FIG. 4A is a view showing an equivalent circuit according to the embodiment.
Figure 4B:
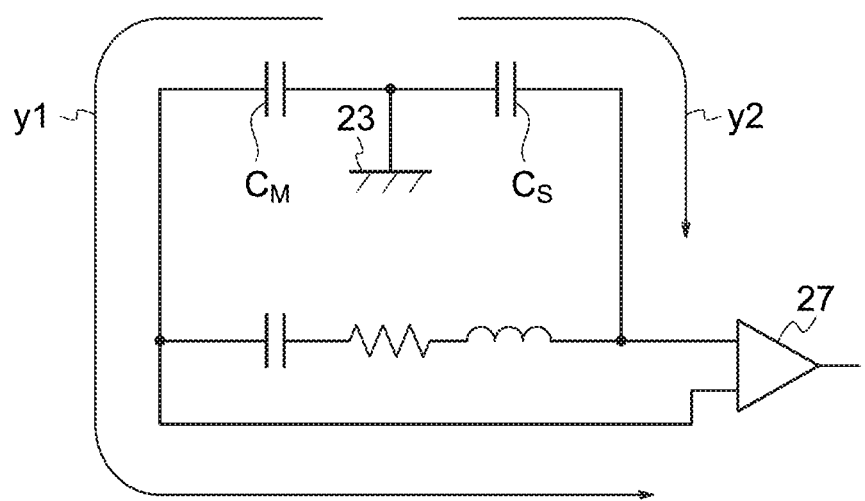
FIG. 4B is a view showing an equivalent circuit of a sensor according to a comparative example.

FIG. 4A is a view showing an equivalent circuit of the sensor 1, and FIG. 4B is a view showing an equivalent circuit of a sensor according to a comparative example.

In the sensor according to the comparative example in FIG. 4B, unlike the sensor 1 explained with reference to FIG. 3, the two element parts 2 are not connected to each other. It is also possible to grasp FIG. 2B used in the explanation of the element part 2 as showing the sensor according to the comparative example.

The equivalent circuit of the sensor (element part 2) according to the comparative example can be represented by for example a serial resonance circuit (notation omitted) configured by capacitors, a resistor, and inductor, capacitors $C_M$ and $C_S$ which are connected in parallel to this serial resonance circuit, and the reference potential part 23 connected between the capacitors $C_M$ and $C_S$. Note that, the notations of the capacitors $C_M$ and $C_S$ will be sometimes used as notations indicating capacities. The capacity $C_M$ is the component caused by the main electrode parts 11M which face each other among equivalent parallel capacities. The capacity $C_S$ is the component caused by the sub electrode parts 11S which face each other among equivalent parallel capacities.

Here, it is assumed that a very small noise is generated from the reference potential part 23. In this case, the noise is input to one terminal of the detection part 27 through the capacitor $C_M$ as indicated by an arrow y1 and is input to the other terminal of the detection part 27 through the capacitor $C_S$ as indicated by an arrow y2. Accordingly, by capacities $C_M$ and $C_S$ being different from each other, the noise is input as differential noise to the detection part 27. If the capacities $C_M$ and $C_S$ are made equal to each other, this differential noise is not generated. However, in the case, the design becomes limited, for example, the areas of the main electrode part 11M and the sub electrode part 11S must be made substantially equal.

On the other hand, the sensor 1 according to the embodiment, as shown in FIG. 4A, can be represented by the serial resonance circuit (notation omitted), capacitors $C_{AM}$ and $C_{AS}$ and $C_{BM}$ and $C_{BS}$ which are connected in parallel to the serial resonance circuit, and the reference potential part 23 which is connected between the capacitors $C_{AM}$ and $C_{AS}$ and between the capacitors $C_{BM}$ and $C_{BS}$. Note that, the notations of $C_{AM}$, $C_{AS}$, $C_{BM}$, and $C_{BS}$ will be sometimes used also as the notations indicating capacities. The capacities $C_{AM}$, $C_{AS}$, $C_{BM}$, and $C_{BS}$ are respectively the components caused by the first main electrode part 11AM, first sub electrode part 11AS, second main electrode part 11BM, and second sub electrode part 11BS among the equivalent parallel capacities.

As explained with reference to FIG. 3, between the two element parts 2, electrode parts 11 which are reversed between the top and bottom and inside and outside are connected to each other. Accordingly, in FIG. 4A, the capacitor $C_{AM}$ and the capacitor $C_{BS}$ are connected in parallel between the reference potential part 23 and one terminal of the detection part 27. Further, the capacitor $C_{AS}$ and the capacitor $C_{BM}$ are connected in parallel between the reference potential part 23 and the other terminal of the detection part 27.

Accordingly, when it is assumed that very small noises are generated from the reference potential parts 23, as indicated by the arrows y11 and y13, the noises are input through the capacitors $C_{AM}$ and $C_{BS}$ connected in parallel with each other to one terminal of the detection part 27. Further, as indicated by arrows y12 and y14, the noises are input through the capacitors $C_{AS}$ and $C_{BM}$ connected in parallel with each other to the other terminal of the detection part 27.

Here, a combined capacity of the capacitors $C_{AM}$ and $C_{BS}$ connected in parallel with each other is $C_{AM}+C_{BS}$. In the same way, a combined capacity of the capacitors $C_{AS}$ and $C_{BM}$ connected in parallel with each other is $C_{AS}+C_{BM}$. On the other hand, the two element parts 2 have the same configurations as each other (from another viewpoint, configurations with up and down reverse), and substantially $C_{AM}=C_{BM}$ and $C_{AS}=C_{BS}$ stand. Accordingly, $C_{AM}+C_{BS}=C_{AS}+C_{BM}$.

As a result, for example, the magnitudes of the noise input to one terminal of the detection part 27 and the noise input to the other terminal of the detection part 27 become equal, therefore the probability of appearance as differential noise is reduced. That is, the SN ratio is improved. Further, unlike the comparative example explained with reference to FIG. 4B, it is not necessary to make the areas etc. of the main electrode parts 11M and the sub electrode parts 11S equal in order to reduce the differential noise, therefore the degree of freedom of design of the main electrode parts 11M and sub electrode parts 11S is improved. Due to this, for example, the degree of coincidence between the planar shapes of the region of the vibration part 5a which projects and the region of it which is recessed in the direction of displacement of the vibration part 5a and the planar shapes of the main electrode parts 11M and the sub electrode parts 11S can be improved. Consequently, the oscillation strength and/or reception sensitivity can be improved.

Further, in the present embodiment, the positive side in the direction of polarization in the first region 10A and the positive side in the direction of polarization in the second region 10B are oriented to the same side of the thickness direction (downward in the example in FIG. 3). The first lower electrode layer 7AL has the first lower main electrode part 11ALM having the same planar shape as that of the first upper main electrode part 11AUM and the first lower sub electrode part 11ALS having the same planar shape as that of the first upper sub electrode part 11AUS. The first lower main electrode part 11ALM and the first lower sub electrode part 11ALS are connected. The second upper electrode layer 7BU has the second upper main electrode part 11BUM having the same planar shape as that of the second lower main electrode part 11BLM and the second upper sub electrode part 11BUS having the same planar shape as that of the second lower sub electrode part 11BLS. The second upper main electrode part 11BUM and the second upper sub electrode part 11BUS are connected.

Accordingly, for example, the sensor 1 is not only given the same configuration electrically, but is also given the same configuration structurally. This will be explained in detail in the explanation of the modification (FIG. 6B) which will be explained later.

In the present embodiment, the piezoelectric layer 9, when viewed on a plane, extends between the first upper main electrode part 11AUM and the first upper sub electrode part 11AUS as well as extends between the second lower main electrode part 11BLM and the second lower sub electrode part 11BLS as well.

Accordingly, for example, compared with an aspect (modification (FIG. 6A) which will be explained later) in which the piezoelectric layer 9 is patterned so that the planar shape of the piezoelectric layer 9 becomes the same as the planar shapes of the main electrode parts 11M and sub electrode parts 11S, the influence of precision of the planar shape of the piezoelectric layer 9 exerted upon the capacities $C_{AM}$, $C_{BM}$, $C_{AS}$, and $C_{BS}$ is reduced. As a result, for example, the possibility of the noises from the reference potential parts 23 appearing as differential noise can be reduced.

In the present embodiment, the first upper sub electrode part 11AUS, when viewed on a plane, extends over a range exceeding a semicircle so as to surround the first upper main electrode part 11AUM. The second lower sub electrode part 11BLS, when viewed on a plane, extends over a range exceeding a semicircle so as to surround the second lower main electrode part 11BLM.

Accordingly, for example, the amount of expansion and contraction in a radial direction when voltages are supplied can be made large. Specifically, compared with the aspect in which the sub electrode parts 11S are dispersed so as to surround the main electrode parts 11M (this aspect is also included in the art according to the present disclosure), the regions in the piezoelectric layer 9 which overlap the sub electrode parts 11S easily supply stresses to each other in the circumferential direction. As a result, the regions in the piezoelectric layer 9 which overlap the sub electrode parts 11S become apt to deform in the radial direction due to the Poisson effect. As a result, for example, the transmission strength is improved. Also, the reception sensitivity is improved in the same way.

In the present embodiment, in the first upper sub electrode part 11AUS, the area of overlap on the cavity 13 which the region 10A faces is larger than the area outside of the former. In the second lower sub electrode part 11BLS, the area of overlap on the cavity 13 which the second region 10B faces is larger than the area outside of the former.

Accordingly, for example, in the piezoelectric layer 9, the region overlapping the sub electrode parts 11S becomes easier to directly influence the vibration of the vibration part 5a compared with the aspect in which the area of the part positioned outside of the cavity 13 is larger than the area of the part overlapping the cavity 13 (this aspect is also included in the art according to the present disclosure). As a result, for example, the effect of improvement of the transmission strength and/or reception sensitivity by suitably setting the planar shapes of the sub electrode parts 11S becomes conspicuous.

(Example of Application)

FIG. 5 is a block diagram schematically showing the configuration of an ultrasonic diagnosis device 101 as an example of application of the sensor 1.

The ultrasonic diagnosis device 101 is provided with for example a probe 103 which is made to abut against a patient, a flexible cable 105 which is connected to the probe 103, and a device body 107 which is connected through the cable 105 to the probe 103.

The probe 103 for example has a sensor substrate 109. The sensor substrate 109 has a plurality of sensors 1 which are arranged in the planar direction (D1 axis direction and/or D2 axis direction). Note that, although not particularly shown, the plurality of sensors 1 may be simultaneously formed by processing a wafer for forming the base body 3. From another viewpoint, the base body 3 may be integrally formed over a plurality of sensors 1.

The plurality of sensors 1 may be ones receiving as input the same electrical signals as each other or may be ones receiving as input electrical signals different from each other (for example electrical signals somewhat offset in phases for electronic scanning).

The device body 107 for example has an input part 111 operated by the user (for example doctor or sonographer) and a control part 113 which controls the transmission part 31 based on a signal from the input part 111. The transmission part 31 is one including the driving part 25 explained above and inputs electrical signals to the plurality of sensors 1. The driving part 25 may be provided for each of the sensors 1 or may be provided in common with respect to the plurality of sensors 1.

Further, the device body 107 is provided with an image processing part 115 which performs image processing based on a signal from the reception part 33 and a signal from the control part 113 and with a display part 117 which displays an image based on a signal from the image processing part 115. The reception part 33 is one including the detection part 27 explained above and detects electrical signals from the plurality of sensors 1. The detection part 27 may be provided for each sensor 1 or may be provided in common with respect to the plurality of sensors 1.

By provision of the configuration as described above, the ultrasonic diagnosis device 101 can display a tomographic image of a patient in the display part 117. Note that, parts (for example amplifiers) of the transmission part 31 and reception part 33 may be provided in the probe 103 as well.

(Modifications)

In the following description, various modifications will be explained. Note that, in the following explanation, basically different parts from the embodiment will be explained. The matters which are not particularly referred to are the same as those in the embodiment. Further, in the following description, even when the shapes etc. of the members are different from those in the embodiment, for convenience, sometimes the same notations as those in the embodiment will be used.

(Modification Relating to Piezoelectric Layer)

FIG. 6A is a schematic cross-sectional view showing a sensor 201 (first element part 202A and second element part 202B) according to a modification and corresponds to FIG. 3.

As shown in this view, the piezoelectric layer 9 may have the same planar shapes as the planar shapes of the main electrode parts 11M and sub electrode parts 11S as well. That is, the piezoelectric layer 9 has a main piezoelectric part 210M having the same planar shape as the planar shapes of the main electrode parts 11M and has a sub piezoelectric part 210S having the same planar shape as the planar shapes of the sub electrode parts 11S.

(Modification Relating to Planar Shape of Electrode Layer)

FIG. 6B is a schematic cross-sectional view showing a sensor 301 (first element part 302A and second element part 302B) according to a modification and corresponds to FIG. 3.

As shown in this view, in each element part 302, the electrode layers 7 (in the example shown, a first lower electrode layer 307AL and second upper electrode layer 307BU) given the reference potential may be formed as solid pattern shaped electrodes. That is, these electrode layers 7 need not have the main electrode parts 11M and sub electrode parts 11S.

The first lower electrode layer 307AL for example has an area large enough to overlap at least all of the first upper electrode layer 7AU (same as that in the embodiment). In the same way, the second upper electrode layer 307BU for example has an area large enough to overlap at least all of the second lower electrode layer 7BL (same as that in the embodiment).

More specifically, for example, the first lower electrode layer 307AL and second upper electrode layer 307BU have planar shapes (including areas) the same as that of the cavity 13. And/or, for example, the first lower electrode layer 307AL and second upper electrode layer 307BU are solid pattern shaped electrodes having outer edges which substantially coincide with the outer edges of the sub electrode parts 11S which they face. Further, for example, the first lower electrode layer 307AL and second upper electrode layer 307BU are solid pattern shaped electrodes with outer edges positioned at the outer sides from the cavity 13 and/or the sub electrode parts 11S which they face.

Also, in the present modification, in the same way as the embodiment, the planar shape of the overlapping region of the first upper main electrode part 11AUM and the first lower electrode layer 307AL and the planar shape of the overlapping region of the second lower main electrode part 11BLM and the second upper electrode layer 307BU are the same. Further, the planar shape of the overlapping region of the first upper sub electrode part 11AUS and the first lower electrode layer 307AL and the planar shape of the overlapping region of the second lower sub electrode part 11BLS and the second upper electrode layer 307BU are the same. Consequently, in the same way as the embodiment, the difference between the capacities $C_{AM}$ and $C_{BM}$ is small, and the difference between the capacities $C_{AS}$ and $C_{BS}$ is small.

Note that, the first lower electrode layer 307AL and the second upper electrode layer 307BU for example have the same planar shapes (including areas). However, they may be different from each other as well. Note that, when this modification and the modification in FIG. 6A are combined, for example, the influence of the difference of the planar shapes (areas) of the first lower electrode layer 307AL and the second upper electrode layer 307BU upon the difference between the capacities $C_{AM}$ and $C_{BM}$ and the difference between the capacities $C_{AS}$ and $C_{BS}$ is small.

The connections of the reference potential part 23, driving part 25, and detection part 27 with respect to various electrode parts 11 are the same as those in the embodiment except that the electrode parts 11 connected to the reference potential parts 23 need not be connected to each other.

In the present modification as well, for example, the possibility of noise from the reference potential parts 23 appearing as differential noise can be reduced. Further, the area of the electrode layer connected with the reference potential part 23 becomes larger, therefore the reference potential is stabilized, so reduction of noise itself from the reference potential part 23 is expected.

In the present modification, the relationships between the stacking order of the solid pattern shaped electrode layer (307AL or 307BU), the piezoelectric layer 9, and the not solid pattern shaped electrode layer (7AU or 7BL) and the up-down direction are inverse to each other between the two element parts 2. Accordingly, the two element parts 2 do not have the same structures as each other in flexing to the same side of the up-down direction.

On the other hand, in the embodiment, in each element part 2, due to the upper electrode layer 7U and the lower electrode layer 7L having the same planar shapes, the two element parts 2 have the same structures as each other in relation to flexing to the same side of the up-down direction. As a result, for example, the electrical characteristics in the two types of routes from the reference potential parts 23 to the detection part 27 (the route indicated by the arrows y11 and y13 and the route indicated by the arrows y12 and y14 in FIG. 4) become equal more easily. Consequently, the probability of the noise from the reference potential parts 23 appearing as differential noise can be more suitably reduced.

(Modification Relating to Driving System)

FIG. 7A is a schematic cross-sectional view showing a sensor 401 (first element part 402A and second element part 402B) according to a modification and corresponds to FIG. 3.

In contrast to the sensor 1 in the embodiment, which was a so-called unimorph type, the sensor 401 according to the present modification becomes a so-called bimorph type. That is, the sensor 401 has two piezoelectric layers 9U and 9L which are superposed on each other. The orientations of polarization of these two piezoelectric layers 9U and 9L become inverse to each other as indicated by the white arrows. Note that, in the example shown, the orientations of polarization of the piezoelectric layers 9U and 9L become orientations facing each other. However, naturally they may be oriented backward relative to each other as well.

In such a bimorph type sensor 401 as well, the same effects as those by the sensor 1 in the embodiment are exhibited. For example, between the two element parts 2, by mutual connection of the electrode parts 11 which are reversed between top and bottom and inside and outside, the possibility of noise from the reference potential parts 23 appearing as differential noise can be reduced.

Note that, in the bimorph type, one of the two piezoelectric layers 9U and 9L may be given the same shape as that of the electrode layer 7 as in the modification in FIG. 6A. Further, the shape of the electrode layer according to the modification in FIG. 6B may be applied to the present modification as well.

(Modification Relating to Orientation of Polarization)

FIG. 7B is a schematic cross-sectional view showing a sensor 501 (first element part 502A and second element part 502B) according to a modification and corresponds to FIG. 3.

As shown in this view, the orientations of polarization in the piezoelectric layer 509 may be made inverse to each other between the two element parts 502 as well. In this modification, the electrode parts 11 reversed between inside and outside may be connected to each other and the electrode parts 11 reversed between top and bottom need not be connected. Further, the lower electrode layer 507L given the reference potential is for example formed as a solid pattern shaped electrode covering the two element parts 502. The lower electrode layer 507L has a planar shape that overlaps at least the first upper electrode layer 7AU and the second upper electrode layer 7BU when viewed on a plane.

Such orientations of polarization, for example, when setting the orientations of polarization by control of the orientation etc. of the crystal at the time of formation of the film of the piezoelectric material, can be realized by separately forming the piezoelectric layers between the two element parts 502. Further, in a case where the orientations of polarization are set by polarization process on the piezoelectric material formed by a ferroelectric material, the orientations of polarization can be realized by forming the piezoelectric layer 509 over the two element parts 502, then supplying voltages having inverse orientations to each other to between the two element parts 502.

In the present modification as well, the same effects as those by the sensor 1 in the embodiment are exhibited. For example, the difference of the magnitudes of the equivalent capacities between the two types of routes from the reference potential parts 23 to the detection part 27 is reduced between the two element parts 502 and in turn the probability of noise from the reference potential parts 23 appearing as differential noise is reduced.

Note that, the lower electrode layer 507L may be formed as a solid pattern shaped electrode for each of the element parts 502 as shown in FIG. 6B or may be given shapes that have the main electrode parts 11M and sub electrode parts 11S as in the embodiment. Further, the piezoelectric layer 509 need not be connected between the element parts 502 and may be given the same shapes as those of the main electrode parts 11M and sub electrode parts 11S as in the modification in FIG. 6A. The present modification can be applied to a bimorph type as well.

In the present modification, the first upper electrode layer 7AU, in the same way as the embodiment, is one example of the first upper electrode layer (electrode layer overlapping one side among the positive side and negative side in the direction of polarization in the first element part). The second upper electrode layer 7BU, unlike the embodiment, is one example of the second lower electrode layer (electrode layer overlapping the other side among the positive side and negative side in the direction of polarization in the second element part). The lower electrode layer 507L is one example of the first lower electrode layer (electrode layer overlapping the other side among the positive side and negative side in the direction of polarization in the first element part) and one example of the second upper electrode layer (electrode layer overlapping one side among the positive side and negative side in the direction of polarization in the second element part).

(Modification Relating to Planar Shapes of Cavities Etc.)

Figure 8:
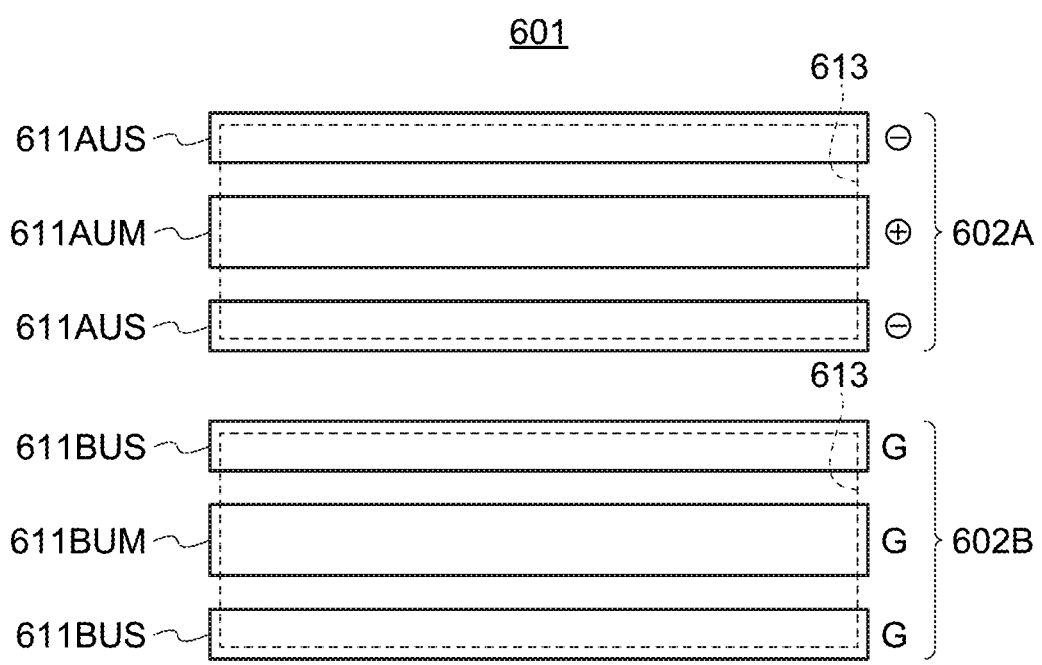
FIG. 8 is a plan view showing the configuration of a sensor according to a modification.

FIG. 8 is a schematic plan view showing a sensor 601 (first element part 602A and second element part 602B) according to a modification.

As shown in this view, the cavities 613 (vibration parts), main electrode parts 611M (ones shown are 611AUM and 611BUM), and sub electrode parts (ones shown are 611AUS and 611BUS) are not limited to circular shapes. Further, the main electrode parts 611M need not be positioned in their entireties on the center side in the cavities 613 either. The sub electrode parts 611S need not surround the main electrode parts 611M either.

In the example shown, the cavities 613 (vibration parts) are rectangular. The main electrode parts 611M are rectangular so as to extend along the lengths of the cavities 613 at the centers of the widths of the cavities 613. The sub electrode parts 611S, on the two sides of the width directions of the cavities 613, are rectangular so as to extend along the lengths of the cavities 613.

The present invention is not limited to the above embodiment or modifications and may be executed in various ways.

As the planar shapes of the cavity (vibration part, first region, second region), main electrode parts, and sub electrode parts, various shapes are possible other than those illustrated. For example, the outer edges of them may be elliptical shapes or may be polygons other than rectangles. The electrode layer and piezoelectric layer were superposed on the membrane on the opposite side to the cavity. However, it is also possible to superpose them on the cavity side.

The sub electrode parts need not fit into the cavity when viewed on a plane. For example, the sub electrode parts may have shapes with inner edges coinciding with the outer edge of the cavity. In this case as well, the vibration part can be made flex by expansion and/or contraction of the piezoelectric layer. Further, the sub electrode parts need not be single continuous shapes, but may be configured by pluralities of divided electrode parts arranged dispersed so as to surround the main electrode parts.

The two element parts configuring the sensor may not be adjacent to each other. That is, another element part may be positioned between the two element parts as well. The number of the element parts which are connected to each other is not limited to two and may be a multiple of two larger than two.

Note that, in a configuration in which both of the upper electrode layer and lower electrode layer (the upper/lower referred to here indicate upper/lower of the D3 axis direction in the same way as the embodiment) in each element part have main electrode parts and sub electrode parts, it is also possible to make the orientations of polarization of the piezoelectric layer inverse to each other between the regions overlapping the main electrode parts and the regions overlapping the sub electrode parts. In this sensor according to the other aspect of the present disclosure, in each element part, the reference potential is given to the main electrode part in one electrode layer of the upper electrode layer and lower electrode layer and to the sub electrode part in the other electrode layer, while the positive and negative potentials are given to between the main electrode part in the other electrode layer and the sub electrode part in the one electrode layer.

REFERENCE SIGNS LIST

1 . . . sensor (ultrasonic sensor), 2A . . . first element part, 2B . . . second element part, 7AU . . . first upper electrode layer, 7AL . . . first lower electrode layer, 7BU . . . second upper electrode layer, 7BL . . . second lower electrode layer, 9 . . . piezoelectric layer, 10A . . . first region, 10B . . . second region, 11AUM . . . first upper main electrode part, 11AUS . . . first upper sub electrode part, 11BLM . . . second lower main electrode part, and 11BLS . . . second lower sub electrode part.

The invention claimed is:

1. An ultrasonic sensor comprising
a piezoelectric layer comprising a first region and a second region which face cavities different from each other and each has a thickness direction as a direction of polarization,
a first element part comprising the first region, and
a second element part comprising the second region, wherein
the first element part comprises
a first upper electrode layer which is located on one side among a positive side and negative side in the direction of polarization relative to the first region and
a first lower electrode layer which is located on the other side among the positive side and negative side in the direction of polarization relative to the first region,
the second element part comprises
a second upper electrode layer which is located on the one side among the positive side and negative side in the direction of polarization relative to the second region and
a second lower electrode layer which is located on the other side among the positive side and negative side in the direction of polarization relative to the second region,
the first upper electrode layer, when viewed on a plane, comprises
a first upper main electrode part comprising a part located on a center side in the first region and
a first upper sub electrode part comprising a part which is located at an outer side of the first region from the first upper main electrode part,
the second lower electrode layer, when viewed on a plane, comprises
a second lower main electrode part comprising a part located on a center side in the second region and
a second lower sub electrode part comprising a part which is located at an outer side of the second region from the second lower main electrode part,
a planar shape of an overlapping region of the first upper main electrode part and the first lower electrode layer and a planar shape of an overlapping region of the second lower main electrode part and the second upper electrode layer are the same,
a planar shape of an overlapping region of the first upper sub electrode part and the first lower electrode layer and a planar shape of an overlapping region of the second lower sub electrode part and the second upper electrode layer are the same,
the first upper main electrode part and the second lower sub electrode part are connected,
the first upper sub electrode part and the second lower main electrode part are connected, and
the first lower electrode layer and the second upper electrode layer are connected.

2. The ultrasonic sensor according to claim 1, wherein:
the positive side in the direction of polarization in the first region and the positive side in the direction of polarization in the second region are oriented to the same side in the thickness direction,
the first lower electrode layer comprises
a first lower main electrode part having the same planar shape as that of the first upper main electrode part and
a first lower sub electrode part having the same planar shape as that of the first upper sub electrode part,
the first lower main electrode part and the first lower sub electrode part are connected,
the second upper electrode layer comprises
a second upper main electrode part having the same planar shape as that of the second lower main electrode part and
a second upper sub electrode part having the same planar shape as that of the second lower sub electrode part, and
the second upper main electrode part and the second upper sub electrode part are connected.

3. The ultrasonic sensor according to claim 1, wherein the piezoelectric layer, when viewed on a plane, expands between the first upper main electrode part and the first upper sub electrode part as well and expands between the second lower main electrode part and the second lower sub electrode part as well.

4. The ultrasonic sensor according to claim 1, wherein:
the first upper sub electrode part extends over a range exceeding a semicircle so as to surround the first upper main electrode part when viewed on a plane, and
the second lower sub electrode part extends over a range exceeding a semicircle so as to surround the second lower main electrode part when viewed on a plane.

5. The ultrasonic sensor according to claim 1, wherein, in the first upper sub electrode part, an area of overlapping the cavity which the first region faces is larger than an area on an outer side thereof, and,
in the second lower sub electrode part, an area of overlapping the cavity which the second region faces is larger than an area on an outer side thereof.

6. The ultrasonic sensor device comprising
an ultrasonic sensor and
a reference potential part, a driving part, and a detection part all connected to the ultrasonic sensor, wherein:
the ultrasonic sensor comprises
a piezoelectric layer comprising a first region and a second region which face cavities different from each other and each has a thickness direction as a direction of polarization,
a first element part comprising the first region, and
a second element part comprising the second region,
the first element part comprises
a first upper electrode layer which is located on one side among a positive side and negative side in the direction of polarization relative to the first region and a first lower electrode layer which is located on the other side among the positive side and negative side in the direction of polarization relative to the first region, the second element part comprises a second upper electrode layer which is located on the one side among the positive side and negative side in the direction of polarization relative to the second region and a second lower electrode layer which is located on the other side among the positive side and negative side in the direction of polarization relative to the second region, the first upper electrode layer, when viewed on a plane, comprises a first upper main electrode part comprising a part located on a center side in the first region and a first upper sub electrode part comprising a part which is located at an outer side of the first region from the first upper main electrode part, the second lower electrode layer, when viewed on a plane, comprises a second lower main electrode part comprising a part located on a center side in the second region and a second lower sub electrode part comprising a part which is located at an outer side of the second region from the second lower main electrode part, a planar shape of an overlapping region of the first upper main electrode part and the first lower electrode layer and a planar shape of an overlapping region of the second lower main electrode part and the second upper electrode layer are the same, a planar shape of an overlapping region of the first upper sub electrode part and the first lower electrode layer and a planar shape of an overlapping region of the second lower sub electrode part and the second upper electrode layer are the same, the reference potential part is connected to the first lower electrode layer and the second upper electrode layer, the driving part can give potentials having inverse polarities to each other with respect to a group of electrodes comprising the first upper main electrode part and the second lower sub electrode part and a group of electrodes comprising the first upper sub electrode part and the second lower main electrode part, and the detection part can detect an electrical signal generated between the two groups of electrodes.

\* \* \* \* \*